(12) United States Patent
Crews et al.

(10) Patent No.: US 11,235,133 B2
(45) Date of Patent: Feb. 1, 2022

(54) SURGICAL INSTRUMENT PORTS CONFIGURED FOR USE WITH WOUND RETRACTORS, AND RELATED DEVICES AND METHODS

(71) Applicant: Intuitive Surgical Operations, Inc., Sunnyvale, CA (US)

(72) Inventors: Brian M. Crews, San Jose, CA (US); Sam T. Crews, Palomar Park, CA (US); Craig R. Gerbi, Half Moon Bay, CA (US); Michael Hurst, San Francisco, CA (US); Sumona Adhya, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 76 days.

(21) Appl. No.: 15/877,867

(22) Filed: Jan. 23, 2018

(65) Prior Publication Data
US 2018/0214681 A1   Aug. 2, 2018

Related U.S. Application Data

(60) Provisional application No. 62/449,826, filed on Jan. 24, 2017.

(51) Int. Cl.
*A61M 39/02* (2006.01)
*A61B 17/34* (2006.01)
(Continued)

(52) U.S. Cl.
CPC ..... *A61M 39/0247* (2013.01); *A61B 1/00154* (2013.01); *A61B 17/3423* (2013.01); *A61B 18/1482* (2013.01); *A61B 17/0218* (2013.01); *A61B 18/1445* (2013.01); *A61B 34/35* (2016.02); *A61B 2017/00526* (2013.01); *A61B 2017/3449* (2013.01); *A61B 2017/3492* (2013.01); *A61B 2018/0063* (2013.01);
(Continued)

(58) Field of Classification Search
CPC .................................................. A61M 39/0247
See application file for complete search history.

(56) References Cited

U.S. PATENT DOCUMENTS

| 4,183,357 A | * | 1/1980 | Bentley | A61F 5/445 604/175 |
| 5,848,992 A | * | 12/1998 | Hart | A61B 17/3423 604/103.03 |
| 7,650,887 B2 | | 1/2010 | Nguyen et al. | |
| 8,623,028 B2 | | 1/2014 | Rogers et al. | |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Tessa M Matthews
(74) *Attorney, Agent, or Firm* — Jones Robb, PLLC (57) ABSTRACT

A surgical port includes an end face with a channel extending through the end face. The channel has a cross section shaped to receive a surgical instrument cannula. A lateral wall extends around a perimeter of the end face. The lateral wall and end face enclose an open volume. A rim extends radially inward from the lateral wall and projects into the open volume. An apron portion extends radially outward from the lateral wall and in a direction axially away from the end face. Surgical systems may include surgical ports. Methods relate to using surgical ports.

25 Claims, 6 Drawing Sheets

(51) Int. Cl.
*A61B 1/00* (2006.01)
*A61B 17/02* (2006.01)
*A61B 18/00* (2006.01)
*A61B 17/00* (2006.01)
*A61B 18/14* (2006.01)
*A61B 34/35* (2016.01)
*A61B 34/30* (2016.01)

(52) U.S. Cl.
CPC ............... *A61B 2018/00077* (2013.01); *A61B 2018/00577* (2013.01); *A61B 2018/00619* (2013.01); *A61B 2034/302* (2016.02); *A61M 2039/0264* (2013.01); *A61M 2039/0267* (2013.01); *A61M 2039/0279* (2013.01); *A61M 2039/0294* (2013.01); *A61M 2207/00* (2013.01)

(56) References Cited

U.S. PATENT DOCUMENTS

| | | | |
|---|---|---|---|
| 8,852,208 B2 | 10/2014 | Gomez et al. | |
| 9,033,995 B2* | 5/2015 | Taylor | A61B 17/00234 606/114 |
| 9,707,011 B2* | 7/2017 | Malkowski | A61B 17/3494 |
| 2010/0228094 A1* | 9/2010 | Ortiz | A61B 17/0293 600/205 |
| 2010/0228096 A1* | 9/2010 | Weisenburgh, II | A61B 17/3462 600/214 |
| 2011/0071473 A1* | 3/2011 | Rogers | A61B 17/3423 604/167.01 |
| 2013/0325031 A1 | 12/2013 | Schena et al. | |
| 2013/0325033 A1 | 12/2013 | Schena et al. | |
| 2017/0361069 A1* | 12/2017 | Gazzani Romolo | A61M 27/00 |

* cited by examiner

SURGICAL INSTRUMENT PORTS CONFIGURED FOR USE WITH WOUND RETRACTORS, AND RELATED DEVICES AND METHODS

RELATED APPLICATIONS

This application claims priority to Provisional U.S. Patent Application No. 62/449,826, filed on Jan. 24, 2017, which is incorporated by reference herein in its entirety.

TECHNICAL FIELD

Aspects of the present disclosure relate to surgical instrument ports configured for use with wound retractors.

INTRODUCTION

Various surgical instruments or tools can be positioned to extend through cannulas passing through an incision in a patient's body wall. Such surgical instruments and tools may be configured for minimally invasive surgical procedures, and can be, without limitation, teleoperated and/or manually controlled. During surgical procedures, it is generally desired to protect the incised edges of the incision from trauma and contamination, as well as in some cases maintain an insufflation pressure at the surgical site. Such functions may be provided, for example, by surgical ports placed within the incision. Such surgical ports are commonly made from an elastic, deformable material, such as, for example, silicone rubber. The ports include passages configured to accept and form a seal around cannulas and/or surgical instruments. Motion of the cannulas may be selectively (i.e., by hardware and/or software configurations) or inherently constrained about a center of motion positioned generally at a midpoint along a longitudinal direction of the surgical port to prevent excessive flexure of the surgical port, which can in turn be transferred to the incision.

During some surgical procedures, wound retractors including an upper retraction ring and a lower retraction ring connected by an annular sheet of protective material are used to seal the incision and hold the incised edges of the incision in an open position. Use of wound retractors during surgical procedures, such as during teleoperated surgical procedures, may provide protection against infection and minimize (e.g., reduce) trauma to the incision and surrounding body wall. However, wound retractors do not generally include provisions for maintaining insufflation pressure or sealing the surgical site against contaminants. A need exists to provide a surgical port that facilitates use of wound retractors with various surgical instruments and maintains insufflation pressure at the surgical site.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical port includes an end face with a channel extending through the end face. The channel has a cross section shaped to receive a surgical instrument cannula. A lateral wall extends around a perimeter of the end face. The lateral wall and end face enclose an open volume. A rim extends radially inward from the lateral wall and projects into the open volume. An apron portion extends radially outward from the lateral wall and in a direction axially away from the end face.

In accordance with at least another exemplary embodiment, a surgical port includes an end face having a perimeter, a lateral wall extending axially from the perimeter, a flexible apron extending radially outward from the lateral wall and axially away from the end face, first and second channels through the end face, an electrically conductive path from the first channel to the apron, and an electrically conductive path from the second channel to the apron.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

The present disclosure contemplates surgical ports having various features configured to interface with wound retractors and components of a surgical system. For example, surgical ports according to the disclosure are configured to couple with wound retractors and include passages configured to accept one or more surgical instrument components, such as one or more surgical instrument cannulas, endoscope cannulas, etc. Surgical ports according to exemplary embodiments of the disclosure include a lower rim extending radially inwardly and configured to interface with a retraction ring of a wound retractor to couple the surgical port with the wound retractor and maintain insufflation pressure within and prevent contamination at the surgical site.

In exemplary embodiments, the surgical port includes an apron portion extending radially outwardly and configured to stabilize the surgical port against the patient's body wall. The surgical port may include passages configured to accept surgical instrument cannulas, and the surgical port may include features around the passages and/or forming the passages that facilitate a wide range of articulation of the cannulas about respective centers of motion of the cannulas while maintaining a seal against the cannulas.

In some exemplary embodiments, the surgical port is made from a material exhibiting a relatively high level of flexibility and a relatively low hardness. For example, and not by way of limitation, the surgical port can be made from a material exhibiting an elongation at break of greater than 100% and a hardness measurement of between 0 and 100 on the shore A hardness scale. In some exemplary embodiments, the surgical port partly or wholly includes materials exhibiting relatively high electrical conductivity. For example, the surgical port in an exemplary embodiment is made of a polymer material, such as silicone rubber, with various additives or other agents that increase the electrical conductivity. The materials exhibiting relatively high electrical conductivity may be configured to form an electrically conductive pathway between electrically conductive cannulas inserted in the port passages, and the body of the patient the port is in contact with, which may be held at a reference (e.g., zero or "body ground") electrical potential. In various exemplary embodiments, the entire surgical port may be made from electrically conductive material, or the surgical port may include portions of electrically conductive material and portions of relatively non-conductive material. Such portions of electrically conductive material serve to dissipate leakage current generated by capacitive coupling that may occur between the surgical instruments. In exemplary embodiments including multiple surgical instruments, separate portions of conductive material, each associated with one or more instruments, may be provided, to electrically isolate one or more surgical instruments from one or more other surgical instruments.

The present disclosure, in various exemplary embodiments, contemplates use of the surgical ports and wound retractors with teleoperated, computer-assisted surgical systems (sometimes referred to as robotic surgical systems). Such systems can include, but are not limited to, those described in, for example, U.S. Patent App. Pub. No. US 2013/0325033 A1, entitled "Multi-Port Surgical Robotic System Architecture" and published on Dec. 5, 2013, U.S. Patent App. Pub. No. US 2013/0325031 A1, entitled "Redundant Axis and Degree of Freedom for Hardware-Constrained Remote Center Robotic Manipulator" and published on Dec. 5, 2013, and U.S. Pat. No. 8,852,208, entitled "Surgical System Instrument Mounting" and published on Oct. 7, 2014, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of surgical ports described herein can optionally be used in conjunction with hand-held, manual surgical instruments and systems.

Figure 1:
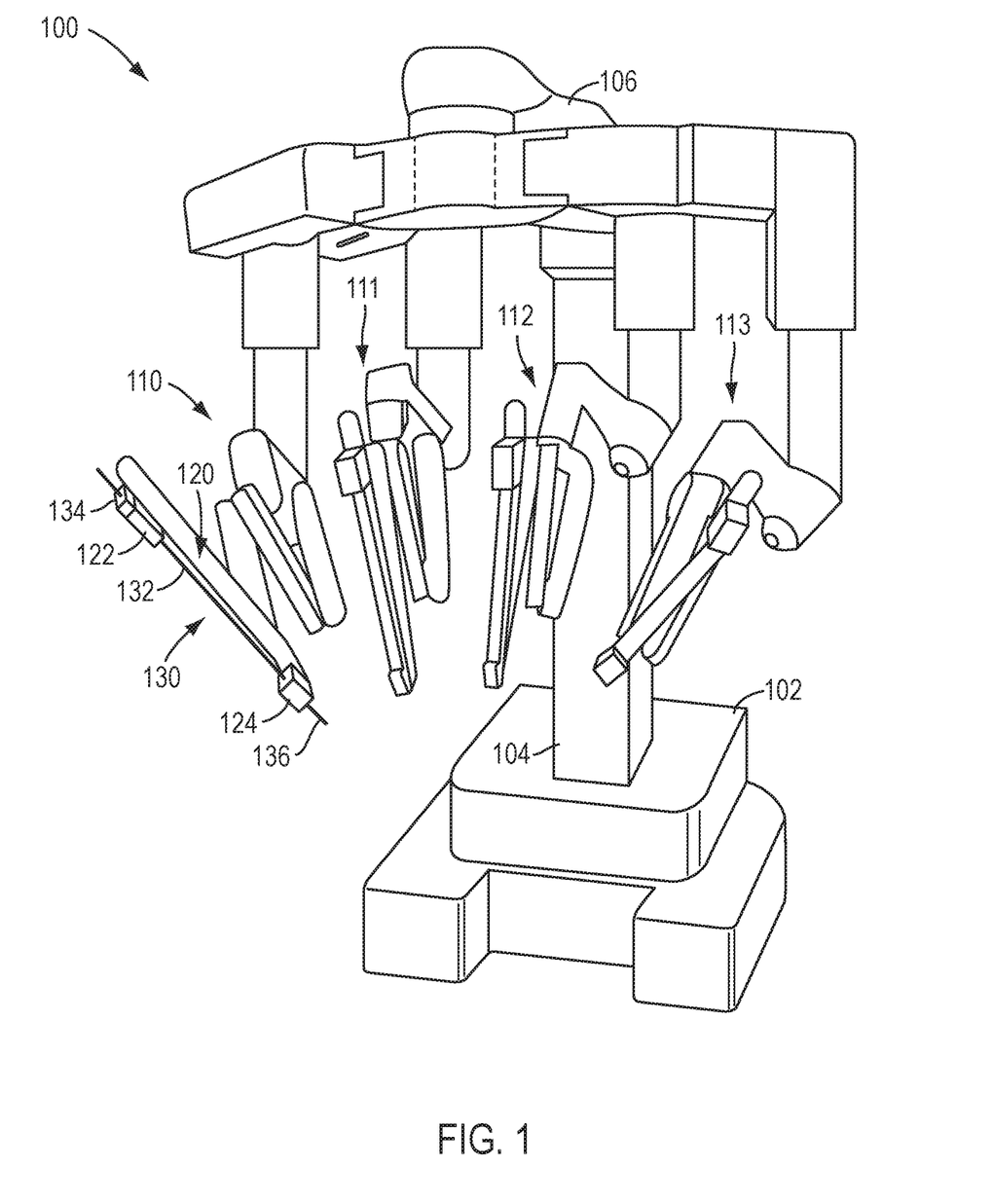
FIG. 1 is a front view of an exemplary embodiment of a patient side cart of a teleoperated surgical system.

As discussed above, in accordance with various exemplary embodiments, surgical instruments of the present disclosure are configured for use in teleoperated, computer-assisted surgical systems (sometimes referred to as robotic surgical systems). Referring now to FIG. 1, an exemplary embodiment of a patient side cart 100 of a teleoperated, computer-assisted surgical system, to which surgical instruments are configured to be mounted for use, is shown. Such a surgical system may further include a surgeon console (not shown) for receiving input from a user to control instruments of patient side cart 100, as well as an auxiliary control/vision cart (not shown), such as those generally described in, for example, the documents incorporated by reference above. Non-limiting, exemplary embodiments of teleoperated surgical systems with which the principles of the present disclosure may be utilized include the available from Intuitive Surgical, Inc. of Sunnyvale, Calif. noted above. However, persons having ordinary skill in the art will appreciate that the present disclosure can be applied to a variety of surgical systems including automated or manual (hand-held) laparoscopic surgical systems, or with other surgical applications.

As shown in the exemplary embodiment of FIG. 1, patient side cart 100 includes a base 102, a main column 104, and a main boom 106 connected to the main column 104. Patient side cart 100 also includes a plurality of arms 110, 111, 112, 113, which are each connected to main boom 106. Arms 110, 111, 112, 113 each include an instrument mount portion 120 to which a respective instrument is mounted, such as instrument 130, which is illustrated as being attached to arm 110. Portions of arms 110, 111, 112, 113 are manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of arm 110 to which the instrument 10 is coupled at the patient side cart 100.

Instrument mount portion 120 comprises an actuation interface assembly 122 and a cannula mount 124, with a force transmission mechanism 134 of the instrument 130 connecting with the actuation interface assembly 122, according to an exemplary embodiment. Cannula mount 124 is configured to hold a cannula 136 through which a shaft 132 of instrument 130 extends to a surgery site during a surgical procedure. Actuation interface assembly 122 contains a variety of drive and other mechanisms that are controlled to respond to input commands at the surgeon console and transmit forces to the force transmission mechanism 134 to actuate the instrument 130.

Figure 3:
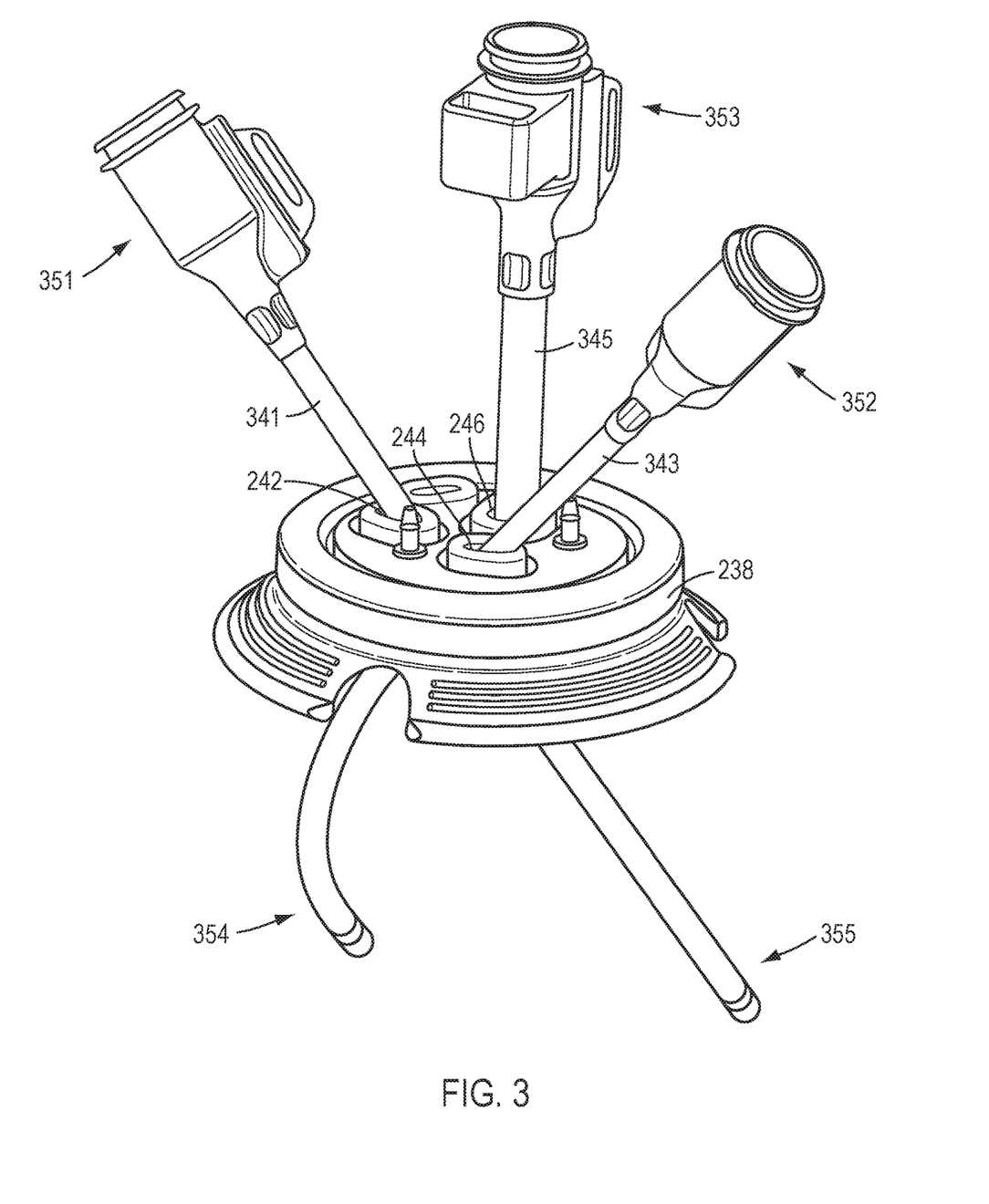
FIG. 3 is a perspective view of the surgical port of FIG. 2, with surgical instrument cannulas inserted through the port according to an exemplary embodiment.

Although the exemplary embodiment of FIG. 1 shows an instrument 130 attached to only arm 110 for ease of viewing, an instrument may be attached to any and each of arms 110, 111, 112, 113. The instrument 130 is a surgical instrument with an end effector. A surgical instrument with an end effector may be attached to and used with any respective one of arms 110, 111, 112, 113. However, the embodiments described herein are not limited to the exemplary embodiment of FIG. 1 and various other teleoperated, computer-assisted surgical system configurations may optionally be used with the exemplary embodiments described herein. Further, the configuration and positioning of each of various components of the patient side cart 100 as shown in FIG. 1, such as the arms 110, 111, 112, 113 is not necessarily representative of the configuration and positioning that is required for use with particular embodiments of the present disclosure. For example, in embodiments of the disclosure configured for use with surgical systems with multiple surgical instruments inserted into a patient's body through a single incision, e.g., as shown in FIG. 3, the configuration, positioning, and orientation of various components of the patient side cart 100, such as the arms 110, 111, 112, 113, are different from that shown in FIG. 1.

Figure 2:
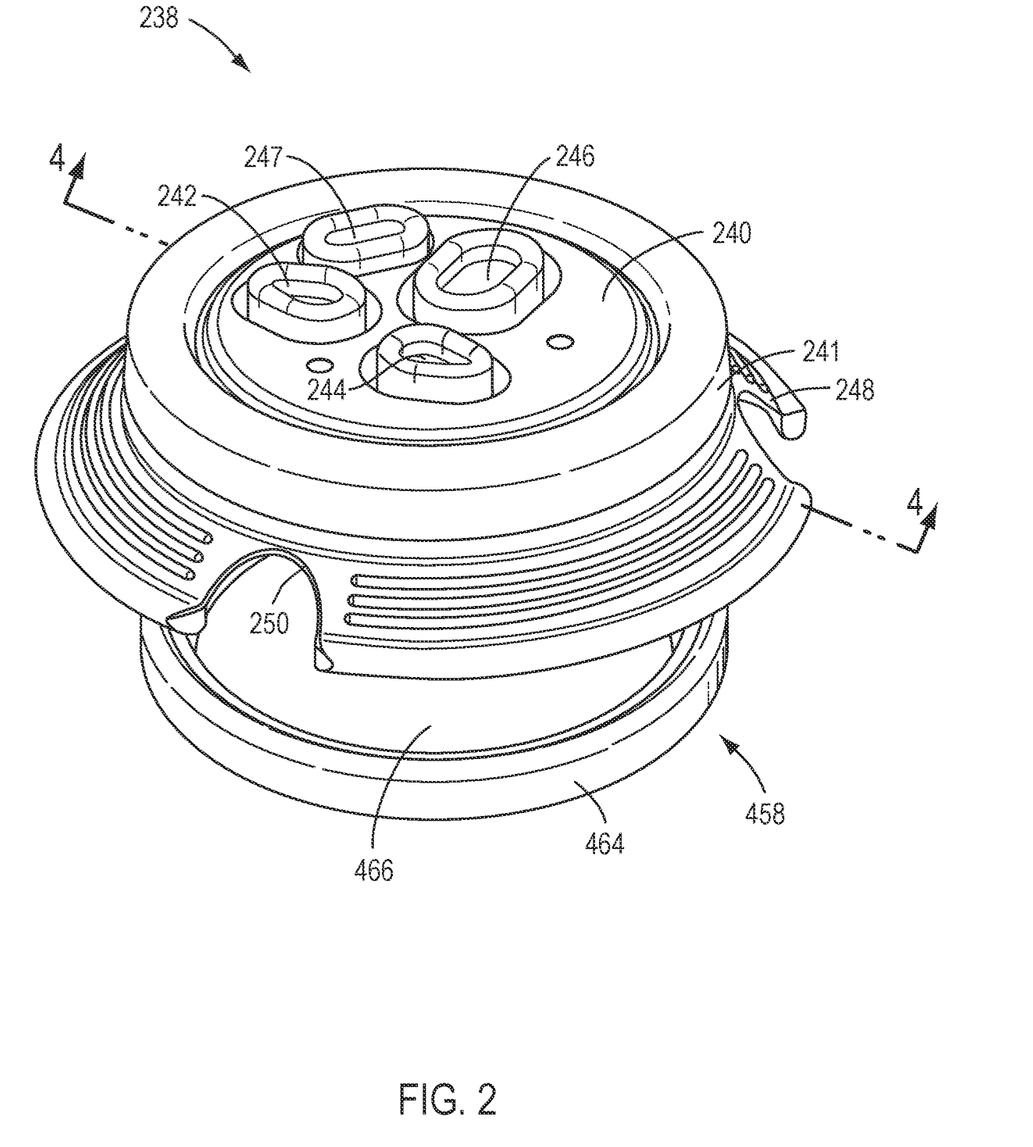
FIG. 2 is a perspective view of a surgical port and wound retractor according to an exemplary embodiment of the disclosure.

Referring now to FIG. 2, an exemplary embodiment of a surgical port 238 is shown in perspective view. The surgical port 238 includes a central portion 240 defining an end face with one or more passage features, such as sealed channels or orifices 242, 244, and 246, each configured to accept and seal around a surgical cannula, such as surgical cannula 136 (FIG. 1). In the exemplary embodiment of FIG. 2, channels 242 and 244 are configured to accept surgical instrument cannulas, and channel 246 is configured to accept an endoscope cannula, or other imaging device or associated components. The surgical port 238 optionally includes one or more auxiliary channels, such as auxiliary channel 247 configured to, e.g., accept a device for creating and maintaining an insufflation pressure within the surgical site. While the exemplary embodiment of FIG. 2 shows three channels 242, 244, and 246, other exemplary embodiments can include more or fewer channels, channels with different configurations, or other arrangements.

Figure 4:
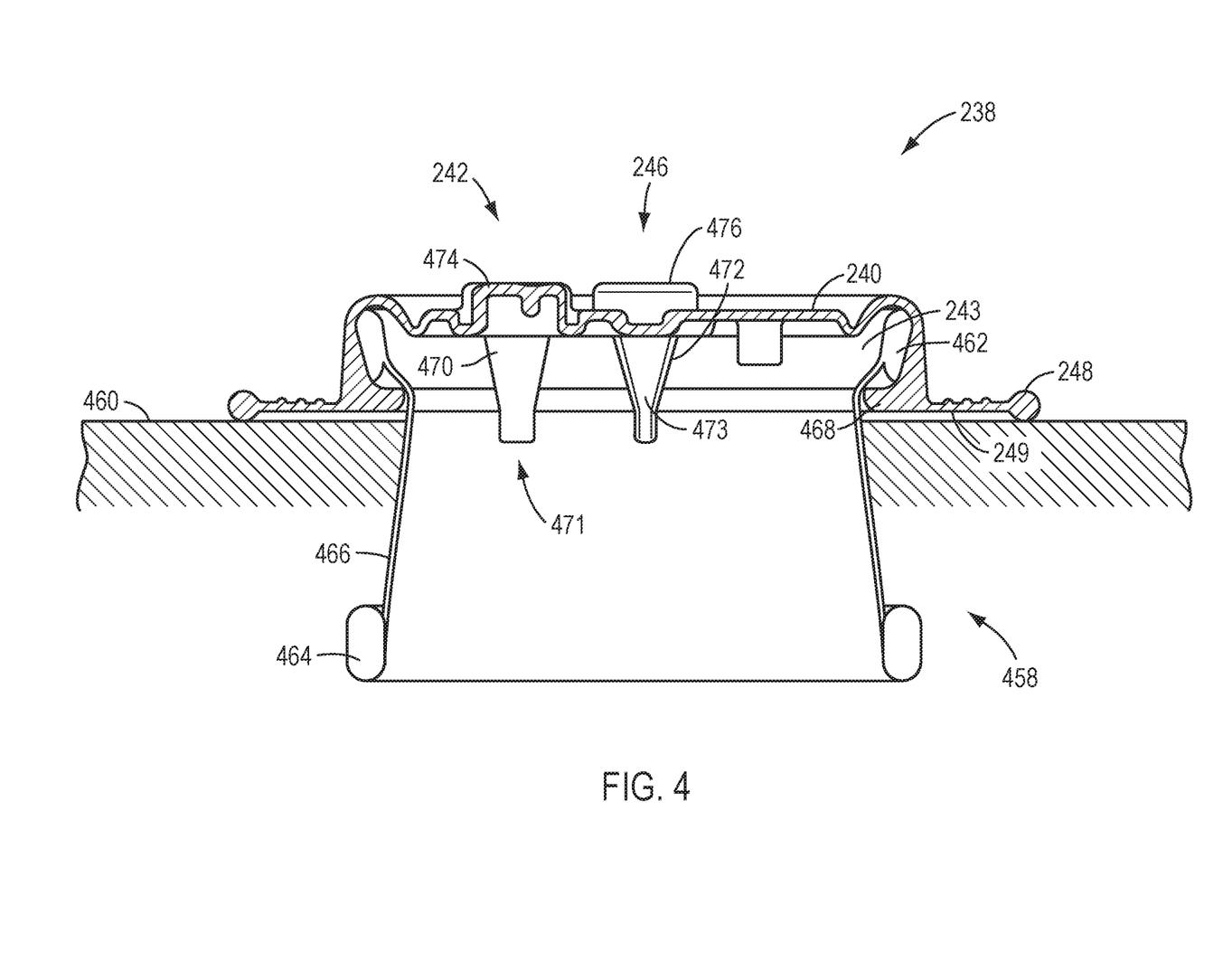
FIG. 4 is a cross-sectional elevation view of a surgical port and wound retractor inserted in an incision according to an exemplary embodiment of the disclosure.

A lateral wall 241 at least partially surrounds a perimeter of the central portion 240, and the central portion 240 and the lateral wall 241 together define an open volume 243 (FIG. 4). In the exemplary embodiment of FIG. 2, the surgical port 238 includes an apron portion 248 extending radially outwardly and axially away from the lateral wall 241 opposite the central portion 240. The apron portion 248 is configured to rest against the body wall (e.g., body wall 460 shown in FIG. 4) when the surgical port 238 is positioned over an incision in the body wall 460 to provide stability to the surgical port 238, as shown below in connection with FIG. 4. The apron portion 248 optionally includes features configured to increase flexibility of the apron portion 248 and ensure that the apron portion 248 forms a contact area with the patient's body wall to impart stability to the surgical port 238. For example, as shown in FIG. 2, the apron portion 248 includes radial reliefs (e.g., cut-outs) 250 configured to enable portions of the apron 248 located circumferentially between the radial reliefs 250 to flex independently of one another to increase (e.g., maximize) contact between the apron 248 and the patient's body wall 460. In addition to stabilizing the surgical port 238 against the patient's body wall 460, contact between the apron portion 248 and the body wall facilitates dissipation of electrical current in exemplary embodiments, such as those shown in FIGS. 5 through 7, in which the surgical port (e.g., surgical port 538, 638, 738) is configured with conductive pathways extending between the channels and the apron portion and configured to dissipate leakage current from conductive cannulas inserted through the ports to a reference potential (e.g., body ground).

Also shown in FIG. 2 is a wound retractor 458 coupled with the surgical port 238. The wound retractor 458 includes an inner ring 464 configured to be positioned within a body wall of a patient. A flexible, annular protective membrane 466 is configured to protect and hold open an incision in the body wall through which the inner ring 464 is inserted. The surgical port 238 is configured to couple with a retraction ring 462 (FIG. 4) of the wound retractor 458 to create a protective barrier around the surgical site and maintain an insufflation pressure at the surgical site. The wound retractor 458 is discussed in further detail below in connection with FIG. 4.

Referring now to FIG. 3, the surgical port 238 is shown in perspective view with cannulas 341, 343, and 345 shown extending through channels 242, 244, and 246, respectively. In the exemplary embodiment of FIG. 3, the cannulas 341 and 343 are configured to accept surgical instruments, such as surgical instruments with end effectors such as forceps, grippers, clamps, shears, clip appliers, staplers, etc. Such end effectors are optionally configured to deliver electrical energy to a surgical site to, e.g., seal, bond, ablate, fulgurate, etc. tissue of the patient. In the exemplary embodiment of FIG. 3, the cannula 345 is configured to accept an imaging device, such as an endoscope. Proximal ends 351, 352, and 353 of cannulas 341, 343, and 345, respectively, are each configured for attachment to a respective cannula mount (e.g., cannula mount 124 in FIG. 1) on a manipulator arm, such as any of manipulator arms 110, 111, 112, and 113 of patient side cart 100 shown in FIG. 1. Distal ends 354 and 355 of cannulas 341 and 343, respectively, are configured to be positioned within an incision in a patient's body wall or otherwise positioned at a surgical site to generally position and guide surgical instruments extending through the cannulas 341 and 343. A distal end of cannula 345 also extends below (in the orientation of FIG. 3) the surgical port 238, but is obscured by the surgical port 238 in the orientation of FIG. 3.

Referring now to FIG. 4, a cross-sectional view (as indicated by section lines 4 on FIG. 2) of the surgical port 238 is shown. The surgical port 238 is shown coupled with a wound retractor 458 positioned in an incision in a body wall 460 of a patient. The wound retractor 458 includes a retraction ring 462 configured to be positioned outside of the body wall 460 and an inner ring 464 configured to be positioned within the body wall 460. A flexible, annular protective membrane 466 extends between the retraction ring 462 and the inner ring 466. The protective membrane 466 seals against the body wall 460 and holds the incision open to allow insertion of surgical instruments, such as surgical instrument 130 (FIG. 1). Wound retractors according to exemplary embodiments of the disclosure may include, but are not limited to, for example, ALEXIS O™ wound protector/retractors available from Applied Medical of Rancho Santa Margarita, Calif., USA. Other wound retractors, such as those manufactured by Applied Medical or by other providers, are also within the scope of the disclosure. For example, various wound retractors are shown and described in U.S. Pat. No. 7,650,887 (filed Jun. 3, 2003) titled "WOUND RETRACTOR," the disclosure of which is herein incorporated by reference in its entirety.

The surgical port 238 includes an inner rim feature 468 extending radially inwardly and configured to interface with (e.g., abut) the retraction ring 462 to couple the surgical port 238 to the wound retractor 458. In the embodiment of FIGS. 2 through 4, the surgical port 238 is manufactured from a relatively resilient material, and is configured to deform (e.g., stretch) to allow the inner rim 468 to be stretched over the retraction ring 462 to secure the surgical port 238 to the retraction ring 462. When the surgical port 238 is coupled with the retraction ring 462, the inner rim 468 of the surgical port 238 engages with and forms a seal against the retraction ring 462. The surgical port 238 and the wound retractor 458 thereby form a protective barrier around the incision of the body wall 460 and maintain an insufflation pressure at the surgical site.

As shown in FIG. 4, when the wound retractor 458 is positioned in the incision and the surgical port 238 is coupled with the wound retractor 458, the apron portion 248 flexes outward from the central portion 240, for example, extending approximately directly radially outward from the central portion 240. A distal surface 249 of the apron portion 248 contacts the patient's body wall 460, thereby imparting stability to the surgical port 238.

In exemplary embodiments of the disclosure, the channels 242, 244, and 246 are formed through features of the surgical port 238 that are configured to seal around the cannulas (e.g., cannula 136 in FIG. 1) of respective surgical instruments (e.g., surgical instrument 130 (FIG. 1)) or imaging devices to maintain insufflation pressure at the surgical site. For example, in the exemplary embodiment of FIG. 4, the channels 242 and 246 are formed as lumens extending through sleeves 470 and 472. Due to the cross-section, channel 244 and associated features are not shown in FIG. 4; however, in the embodiment of FIG. 4, the channel 244 includes features, such as the sleeve and bellows described below, similar to the features of channels 242 and 246.

In the exemplary embodiment of FIG. 4, the sleeves 470 and 472 are formed (e.g., molded) integrally with the central portion 240 of the surgical port 238. The sleeves 470 and 472 each include respective bellows portions 474 and 476 that are configured to impart additional flexibility to the sleeves 470 and 472 to facilitate articulation of the sleeves 470 and 472 as cannulas positioned therein (e.g., cannulas 351, 353 shown in FIG. 3) are manipulated by manipulator arms (such as manipulator arms 110, 111 112, 113) of patient side cart 100 (FIG. 1). Each of the sleeves 470 and 472 may extend from a respective one of the bellows portions 474 and 476 distally toward the apron 248 to surround the cannulas and prevent a loss of insufflation pressure through the passages 242 and 246 around the cannulas. The bellows portions 474 and 476 may be characterized as having a "U-shaped" cross-section.

The sleeves 470 and 472 optionally taper from a wide dimension (e.g., width, diameter, etc.) proximate the respective bellows portions 474 and 476 to a relatively narrow dimension at respective distal ends (e.g., distal end 471 of sleeve 470), as shown in FIG. 4. The relatively wide dimension of at the respective bellows portion may facilitate insertion of a respective cannula within the sleeves 470 and 472, while the narrow distal end (e.g., distal end 471) of the sleeves 470 and 472 ensures a tight fit around the respective cannula to effectively maintain insufflation pressure at the surgical site. The sleeves 470 and 472 optionally include features configured to prevent the sleeves 470 and 472 from inverting (e.g., being pulled at least partially upward and inside-out through a respective one of the channels 242, 246) when the cannulas are Removed from their respective sleeves. For example, the sleeves 470 and 472 may include integrally molded vertical ribs 473. Additionally or alternatively, the sleeves 470 and 472 optionally have a wall thickness sufficient to prevent the sleeves from inverting when the cannulas are removed from the sleeves.

In exemplary embodiments, the surgical port 238 is manufactured from relatively flexible materials such as polymer materials. For example, in an exemplary embodiment, the surgical port is manufactured from silicone rubber. In some situations, if the port material separating various surgical instrument cannulas is sufficiently electrically insulating, there is potential for capacitive coupling to occur between the instruments, resulting in misdirection of electrical energy. The disclosure contemplates various approaches for mitigating such capacitive coupling by dissipating electrical energy from the cannulas and associated surgical instruments to the body of the patient.

For example, in some exemplary embodiments, the entire surgical port 238 is manufactured from a polymer material exhibiting electrically conductive characteristics, such as silicone rubber with one or more additives that increase electrical conductivity, such as, e.g., carbon particles, carbon fibers, nickel-plated carbon fibers, nano-scale carbon materials such as carbon nanotubes, or other additives.

In an exemplary embodiment, carbon is added to silicone rubber in the form of carbon fiber rods distributed throughout the material of the surgical port. For example, the carbon fiber rods may be incorporated into the material substantially as described in U.S. Provisional Patent Application No. 62/449,822, filed on Jan. 24, 2017, titled SURGICAL INSTRUMENT PORTS WITH ELECTRICALLY CONDUCTIVE PORTIONS, RELATED DEVICES, AND RELATED METHODS, the entire contents of which are incorporated by reference herein.

In particular, in an exemplary embodiment, carbon fiber rods are mixed with silicone rubber raw materials prior to the molding process. As described in greater detail in U.S. Provisional Patent Application No. 62/449,822, the carbon fiber rods prior to mixing have a length of several millimeters (mm), such ranging from 1 mm to 20 mm, and a diameter of several micrometers (μm), such as ranging from 5 μm to 15 μm. In one exemplary embodiment, the carbon fiber rods have a length of 12-13 mm prior to mixing and a diameter of 10 μm. As further non-limiting examples, the carbon fiber rods before mixing with the silicone rubber raw materials exhibit a length to diameter ratio of greater than 5:1, greater than 10:1, greater than 20:1, greater than 50:1, greater than 100:1, etc.

As a non-limiting example, the carbon fiber rods exhibit a tensile strength of greater than 1000 MPa (145,000 psi). As a more specific non-limiting example, the carbon fiber rods exhibit a tensile strength of 1207 MPa (175000 psi). In some embodiments, the tensile strength may exceed 3000 MPa, 4000 MPa, or more. According to an exemplary embodiment, the carbon fiber rods exhibit a tensile modulus (i.e., elastic modulus under tensile stress conditions) of greater than 100 GPa (14,500 kpsi). For example, in an exemplary embodiment, the carbon fiber rods exhibit a tensile modulus of 137 GPa (20,000 kpsi). In some embodiments, the tensile modulus may exceed 175 GPa, 200 GPa, or more.

According to various exemplary embodiments, the carbon fiber rods are mixed with the silicone rubber raw materials at a volume percent ranging from 1 volume percent (vol %) to 10 vol %, for example from 4 vol % to 5 vol %. In some exemplary embodiments, the carbon fiber rods are mixed with the silicone rubber raw materials at a weight percent ranging from 0.1 weight percent (wt %) to 5 wt %, for example the weight percent can be 1.5 wt %.

The weight or volume percent of carbon fiber added to the silicone rubber is dependent at least partly on the tensile modulus of the carbon fibers. Stronger carbon fibers (e.g., those with a higher tensile modulus) are less likely to break during mixing with the silicone rubber raw materials, resulting in longer lengths of carbon fiber rods in the final molded component. This can result in more ready formation of electrically conductive networks with one another and result in enhanced overall electrical conductivity of the final component for a given weight or volume percent of the carbon fiber rods. Conversely, weaker carbon fiber rods break into smaller lengths during mixing and do not form conductive networks with one another as readily due to their shorter length, and thereby can result in relatively lower electrical conductivity for a given weight or volume percent, as compared to a stronger carbon fiber. Sufficient tensile modulus, such as the ranges of tensile modulus values noted above, and sufficient starting length of the carbon fiber rods can help to ensure that the carbon fiber rods maintain, on average, a length of greater than 1 mm, or greater than 3 mm, greater than 5 mm, etc. In exemplary embodiments, the carbon fiber rods exhibit an average post-mixing length ranging from 6 mm to 12 mm.

Carbon fibers suitable for use in disclosed exemplary embodiments are available from suppliers such as, for example, Toho Tenax America, Inc., Rockwood, Tenn., USA; Cytec Industries Inc., Woodland Park N.J., USA; and Asbury Carbons, Asbury, N.J., USA. Some carbon fibers are supplied with sizing treatments (i.e., a chemical coating over the fiber that improves bonding of the fiber with the resins or other polymers typically used in carbon fiber composite materials) that may potentially interfere with (e.g., reduce) the electrical conductivity between the carbon fiber rods once the carbon fiber rods are incorporated into the silicone rubber material. Accordingly, in some exemplary embodiments, any sizing present on the carbon fiber rods is removed from the rods prior to mixing with the silicone rubber material to promote electrical conductivity between the carbon fiber rods. For example, the carbon fiber rod particles are immersed in a solvent under low pressure conditions (e.g., within a vacuum chamber) to remove the sizing.

Embodiments of surgical ports manufactured from electrically conductive materials form a common path between each conductive cannula and the body ground. However, in some situations, it may be desirable to provide separate pathways between one or more of the surgical and/or imaging instruments to the body ground. Accordingly, in some exemplary embodiments, a surgical port is configured to include separate pathways between the surgical instruments and/or the imaging instruments. Stated another way, the surgical port may be configured to electrically isolate the surgical instruments from the imaging instruments, to isolate various groups of surgical instruments from one another, to isolate each instrument from each other instrument, or combinations thereof.

Figure 5:
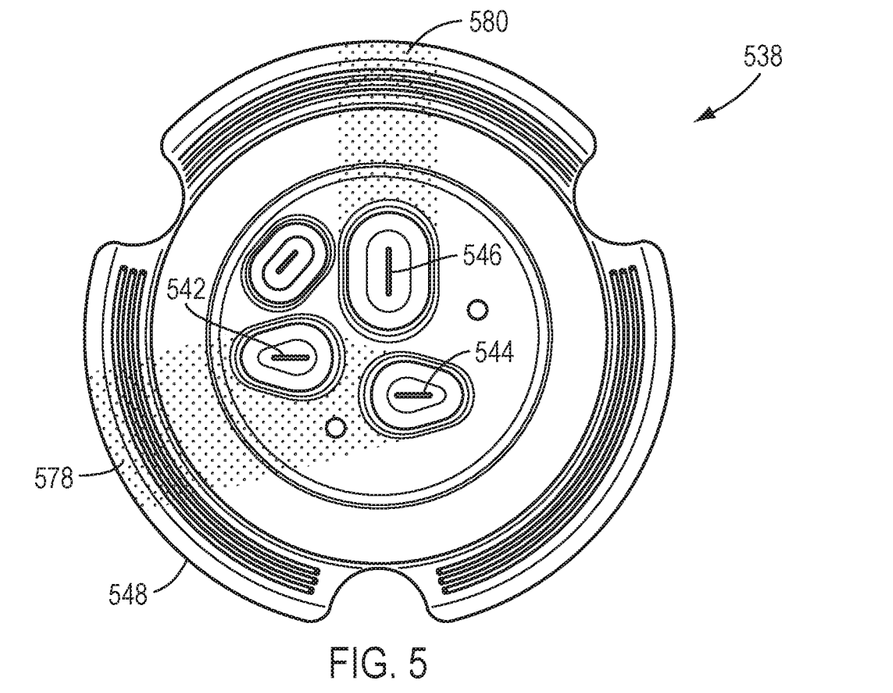
FIG. 5 is a plan view of a surgical port according to another embodiment of the disclosure.
Figure 6:
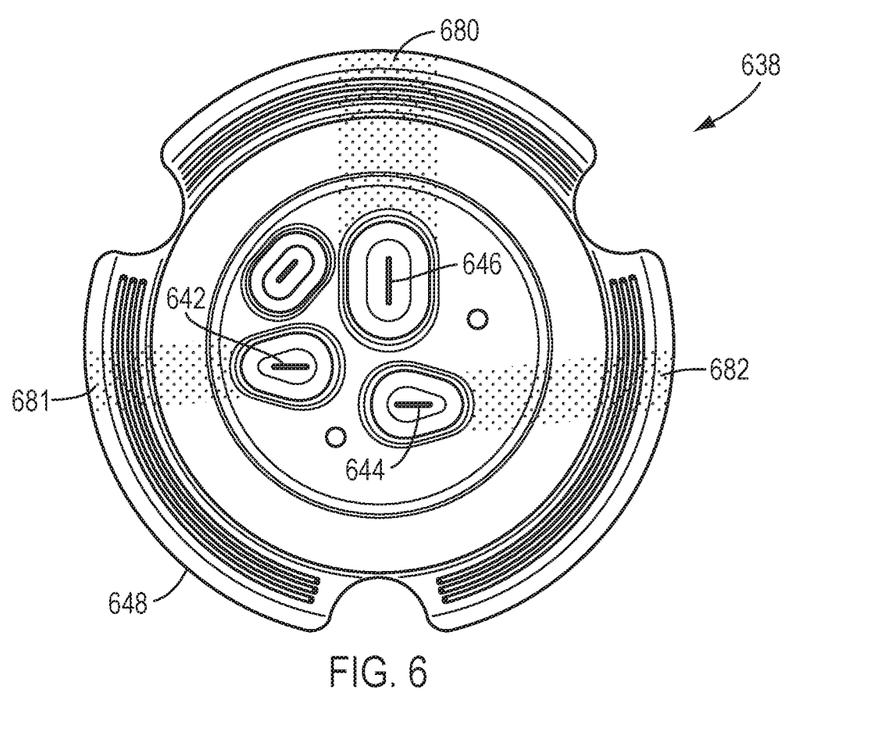
FIG. 6 is a plan view of a surgical port according to yet another exemplary embodiment of the disclosure.

For example, referring now to FIG. 5, a surgical port 538 includes conductive pathways 578 and 580 of relatively conductive material extending between channels 542, 544, and 546 and apron 548. When conductive cannulas (such as cannulas 351, 352, and 353 shown in FIG. 3) are each positioned within the channels 542, 544, and 546, the conductive pathways 578, 580 dissipate electrical energy from the cannulas to the apron 548 (e.g., to a distal surface of the apron 548, corresponding to distal surface 249 of apron 248 in FIG. 4) and to the body of the patient, which may be held at a reference potential (e.g., zero electrical potential, body ground, etc.) by connection with a patient return pad or other grounding electrode. The conductive pathways 578, 580 extend into each respective channel 542, 544, and 546 to ensure contact with respective cannulas that are inserted in the channels. The conductive pathways 578, 580 extend around an outer edge of the apron 548 and onto a distal portion of the apron 548 (i.e., a portion of the apron facing the surface of the body wall 460 (FIG. 4)) to ensure conductive contact occurs between the conductive pathways 578, 580 and the body wall 460 when the surgical port 538 is positioned over the wound retractor 458.

In the exemplary embodiment of FIG. 5, the pathways 578 and 580 are coatings formed on a surface of the surgical port 538. In other words, the surgical port 538 is molded of a relatively non-conductive material, similar to surgical port 238, and the pathways 578, 580 are formed by coating the relatively non-conductive material with a relatively conductive surface coating. For example, in one embodiment, the pathways 578, 580 are formed by coating the surface of the surgical port 538 with a conductive material, such as a paint or other coating with electrically conductive characteristics. For example, such a coating can include particles of metallic material, carbon, or other conductive material dispersed within a matrix material that binds the particles together and to the surface of the surgical port 538.

In another exemplary embodiment, the pathways 578 and 580 are formed after molding a portion of the surgical port 538 from material having relatively low electrical conductivity (e.g., silicone rubber without additives for increasing the electrical conductivity). The relatively low-conductivity portion is overmolded with material having relatively higher electrical conductivity (e.g., silicone rubber with additives, such as carbon fiber rods or other materials for increasing the electrical conductivity of the material) to form the conductive pathways 578 and 580. As non-limiting examples, molding the low-conductivity and high-conductivity portions of the surgical port 538 is accomplished by injection molding or other molding methods, by casting, additive manufacturing processes, or any other manufacturing process.

In the embodiment of FIG. 5, the pathway 578 creates a common conductive path between the apron 548 and the channels 542 and 544, while the pathway 580 creates a separate conductive path between the channel 546 and the apron 548. Electrically isolating the channels in this manner, i.e., by configuring the conductive paths with portions of non-conductive material of the surgical port 538 between the conductive paths, facilitates decoupling of one or more surgical instruments from one or more other instruments or devices. For example, in some situations it is desired to provide separate conductive pathways for various different instruments to prevent (e.g., mitigate) capacitive coupling between the instruments. As a non-limiting example, isolation of an endoscope or other imaging instrument from other surgical instruments is desirable. Accordingly, in the embodiment of FIG. 5, the channels 542 and 544 are configured to accept surgical instruments, while the channel 546 is configured to accept an endoscope or other imaging instrument.

In other embodiments, separate conductive paths are formed between each of the channels and the apron. For example, in the surgical port 638 shown in FIG. 6, pathways 680, 681, and 682 create separate conductive paths between each of channels 642, 644, and 646 and the apron 648. Thus, each instrument and associated conductive cannula positioned in each of the channels 642, 644, and 646 is independently brought into electrical communication with the patient's body through contact between the body and the apron 648, thereby preventing (e.g., mitigating) any capacitive coupling between the various instruments.

Figure 7:
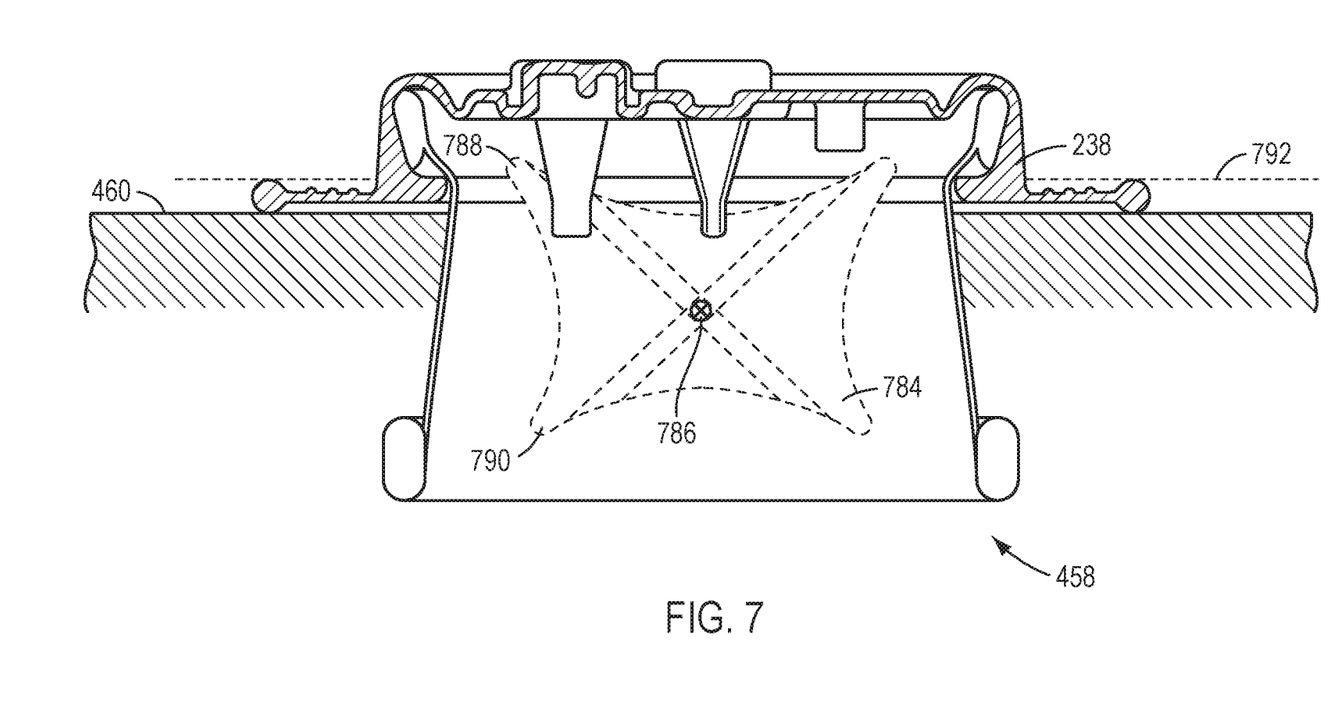
FIG. 7 is a cross-sectional elevation view of a prior art surgical port superimposed over a surgical port according to another exemplary embodiment of the disclosure.

Surgical ports according to exemplary embodiments of the disclosure can provide additional flexibility in positioning and manipulation of surgical instruments. For example, surgical ports 238, 538, and 638 of the disclosure facilitate positioning a center of motion of each of the surgical instruments (i.e., a local region along the cannula length about which the cannula and associated instrument is manipulated in one or more degrees of freedom, such one or more of pitch, roll, and yaw) generally aligned with, or even above, a surface of the patient's body wall (e.g., body wall 460 shown in FIG. 3). With reference now to FIG. 7, a prior art surgical port 784 is shown superimposed (in dashed outline) over a surgical port 238 of the disclosure to compare placement of the ports relative to a body wall 460. Due to the inherent stiffness of the material of the surgical port 784, a center of motion 786 of the instruments is placed near the vertical center of the port (i.e., a midpoint between an upper flange 788 and a lower flange 790) to minimize required deformation of the port 784 as the instrument(s) are manipulated about the center of motion 786. Thus, in the example of FIG. 7, the geometry of the port 784 requires the center of the port 784 to generally align with a vertical midpoint of the body wall 460. The surgical port 238 configured for use with wound retractors according to exemplary embodiments of the disclosure facilitates placement of a center of motion along a line 792 closer to, or above, the surface of the patient's body wall 460, because the area within the wound retractor accommodates greater motion of the cannulas compared to the surgical port 784. In addition, embodiments of the surgical ports 238, 438, 538 of the disclosure are potentially thinner and more flexible for a given durometer measurement as compared to the surgical port 784, thereby permitting a greater range of articulation of the surgical instruments.

In addition, because the geometry of the ports 238, 538, 638 is less limiting to articulation of the surgical instruments compared to the surgical port 784, relatively higher material stiffness has less detrimental effect on the articulation of the surgical instruments. This characteristic of exemplary embodiments of ports of the disclosure facilitates forming the ports entirely from electrically conductive material. For example, additives can be used to alter the electrical conductivity characteristics of polymer materials, such as materials used to manufacture the surgical ports 238, 538, 638, but such additives potentially alter the mechanical characteristics of the material. For example, added carbon particles increase the electrical conductivity of silicone rubber material, but also tend to increase the stiffness (e.g., increase the hardness as measured by a durometer test), for example, of the silicone rubber material into which the particles are integrated. Because the ports 238, 438, 538 provide geometry and features to facilitate articulation of the surgical instruments, such as the bellows 368, 369, 370 (FIG. 3), and the generally thin and planar central portion 240, an increase in material stiffness resulting from conductive additives potentially has a lesser adverse effect on articulation of the surgical instruments than does a similar increase of stiffness of the material in the solid port 784. As specific, non-limiting examples, a non-conductive silicone rubber material used for surgical ports can exhibit a durometer measurement of 10 on the Shore A scale, while a silicone rubber material with conductive additives can exhibit durometer measurements in a range of 15-20 on the Shore A scale. These examples are provided for illustration only, and some non-conductive silicone rubber materials exhibit a durometer measurement of less than or greater than 10 on the Shore A scale, and some silicone rubber materials with conductive additives exhibit durometer measurements outside the range of 15-20 on the Shore A scale.

Surgical ports according to exemplary embodiments of the disclosure are configured for use with wound retractors and facilitate using wound retractors with various teleoperated surgical systems. Surgical ports according to various exemplary embodiments of the disclosure facilitate dissipation of leakage current (e.g., due to capacitive coupling) to a body ground or other reference potential. Finally, exemplary embodiments of surgical ports of the disclosure provide additional flexibility compared to solid port designs, and permit positioning of centers of motion of surgical instruments closer to (e.g., aligned with) or above a surface of a body wall.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A surgical port, comprising:
   an end face having a perimeter and defining a radial orientation of the surgical port along the end face and an axial orientation of the surgical port normal to the end face;
   a channel extending through the end face, the channel having a cross section shaped to receive a surgical instrument cannula;
   a lateral wall extending around the perimeter of the end face, the lateral wall having a perimeter, and the lateral wall and the end face together enclosing an open volume;
   a rim extending from the lateral wall radially inward into the open volume; and
   an apron portion extending around an entirety or substantially an entirety of the perimeter of the lateral wall, the apron portion being deflectable from a first position in which the apron portion extends radially outward relative to the lateral wall and axially away from the end face to a second position in which the apron portion is deflected in a direction axially toward the end face and radially outward relative to the first position.

2. The surgical port of claim 1, wherein:
   the rim is shaped to engage with a wound retractor device received in the open volume.

3. The surgical port of claim 1, wherein:
   the surgical port further comprises a wound retractor device received in the open volume and engaged with the rim.

4. The surgical port of claim 1, wherein:
   the surgical port further comprises a sleeve extending from the end face into the open volume; and
   the channel extends through the sleeve.

5. The surgical port of claim 4, wherein:
   the sleeve extends axially beyond the rim.

6. The surgical port of claim 4, wherein:
   the sleeve is tapered in a direction extending away from the end face into the open volume.

7. The surgical port of claim 1, wherein:
   the surgical port further comprises a bellows portion defining a portion of the channel.

8. The surgical port of claim 1, wherein:
   the apron portion comprises an outer perimeter and a relief extending radially inward from the outer perimeter.

9. The surgical port of claim 8, wherein:
   the apron portion comprises a perimeter;
   the relief is one relief of a plurality of reliefs spaced around the perimeter of the apron portion; and
   the plurality of reliefs divides the apron portion into a plurality of arc segments.

10. The surgical port of claim 1, wherein:
    the lateral wall comprises a free end and extends from the end face to the free end of the lateral wall; and
    the apron portion extends from the free end of the lateral wall.

11. The surgical port of claim 1, wherein:
    the surgical port further comprises a second channel extending through the end face;
    the second channel has a cross section shaped to receive a cannula associated with an endoscopic imaging device; and
    the cross section of the second channel is different from the cross section of the channel.

12. The surgical port of claim 1, wherein:
    the surgical port comprises electrically conductive material.

13. The surgical port of claim 1, wherein:
    the surgical port comprises electrically conductive particles dispersed in silicone rubber.

14. The surgical port of claim 1, wherein:
    the surgical port comprises rod-shaped particles of carbon-fiber dispersed in silicone rubber.

15. The surgical port of claim 1, wherein:
    the surgical port comprises electrically insulating material.

16. The surgical port of claim 15, wherein:
    the surgical port further comprises an electrically conductive material path on the electrically insulating material;
    the channel is defined by a surface; and
    the electrically conductive material path extends between the apron portion and the surface defining the channel.

17. The surgical port of claim 15, wherein:
    the surgical port comprises a first surface defining the channel, a second surface defining a second channel extending through the end face, and an electrically conductive material path;
    the second channel has a cross section shaped to receive a second cannula associated with a second surgical instrument or an endoscopic imaging device; and
    the electrically conductive material path extends between the first surface, the second surface, and the apron portion.

18. The surgical port of claim 15, wherein:
    the surgical port comprises a first surface defining the channel, a second surface defining a second channel extending through the end face, a first electrically conductive material path, and a second electrically conductive material path;
    the second channel has a cross section shaped to receive a second cannula associated with a second surgical instrument or an endoscopic imaging device;
    the first electrically conductive material path extends between the first surface and the apron portion;

the second electrically conductive material path extends between the second surface and the apron portion; and the second electrically conductive material path is separate from the first electrically conductive material path.

19. The surgical port of claim 1, wherein:

the apron portion comprises a free end that moves radially outwardly in response to radial outward deflection of the apron portion relative to the lateral wall.

20. The surgical port of claim 1, wherein:

the apron portion extends from the lateral wall radially away from the end face.

21. A surgical port comprising:

an end face having a first perimeter and defining a radial orientation of the surgical port along the end face and an axial orientation of the surgical port normal to the end face;

a lateral wall having a second perimeter and extending axially from the first perimeter of the end face;

a flexible apron portion extending around an entirety or substantially an entirety of the second perimeter of the lateral wall, extending radially outward from the lateral wall, and extending axially away from the end face;

first and second channels through the end face;

an electrically conductive path from the first channel to the apron portion; and an electrically conductive path from the second channel to the apron portion.

22. The surgical port of claim 21, wherein:

the electrically conductive path from the first channel to the apron portion and the electrically conductive path from the second channel to the apron portion are separate paths electrically insulated from one another.

23. The surgical port of claim 22, wherein:

the end face, the lateral wall, and the flexible apron portion each comprise an electrically insulating material; and the electrically conductive path from the first channel to the apron portion and the electrically conductive path from the second channel to the apron portion each comprise carbon fiber rods without sizing and having an average length in a range of 6-12 mm range mixed with silicone rubber at a range of 1-10 percent by volume.

24. A medical device comprising:

an end face;

a channel through the end face; and an electrically conductive path extending from the channel and comprising carbon fiber rods without sizing and having an average length in a range of 6-12 mm range mixed with silicone rubber at a range of 1-10 percent by volume.

25. The medical device of claim 24, wherein:

the medical device further comprises an apron portion surrounding the end face; and the electrically conductive path extends from the channel to the apron portion.

* * * * *